(12) United States Patent
Thornton

(10) Patent No.: US 7,682,385 B2
(45) Date of Patent: Mar. 23, 2010

(54) ARTIFICIAL VALVE

(75) Inventor: Sally C. Thornton, Marlborough, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 11/480,717

(22) Filed: Jul. 3, 2006

(65) Prior Publication Data

US 2006/0253189 A1 Nov. 9, 2006

Related U.S. Application Data

(63) Continuation of application No. 10/873,052, filed on Jun. 22, 2004, now Pat. No. 7,081,131, which is a continuation of application No. 10/115,557, filed on Apr. 3, 2002, now Pat. No. 6,752,828.

(51) Int. Cl.
A61F 2/04 (2006.01)
A61F 2/24 (2006.01)

(52) U.S. Cl. .................. 623/1.24; 623/2.12; 623/23.68

(58) Field of Classification Search ................ 623/1.24, 623/1.25, 1.26, 2.12, 2.13, 2.14, 2.15, 2.16, 623/23.68
See application file for complete search history.

(56) References Cited

U.S. PATENT DOCUMENTS

| 3,671,979 | A | | 6/1972 | Moulopoulos | 3/1 |
| 4,218,782 | A | * | 8/1980 | Rygg | 623/2.15 |
| 4,291,420 | A | | 9/1981 | Reul | 3/1.5 |
| 4,787,901 | A | | 11/1988 | Baykut | 623/2 |
| 4,872,874 | A | | 10/1989 | Taheri | 623/1 |
| 4,935,030 | A | | 6/1990 | Alonso | 623/2 |
| 4,994,077 | A | | 2/1991 | Dobben | 623/2 |
| 5,002,567 | A | | 3/1991 | Bona et al. | 623/2 |
| 5,141,491 | A | | 8/1992 | Bowald | 604/22 |
| 5,163,953 | A | | 11/1992 | Vince | 623/2 |
| 5,219,355 | A | | 6/1993 | Parodi et al. | 606/191 |
| 5,254,127 | A | | 10/1993 | Wholey et al. | 606/153 |
| 5,327,774 | A | | 7/1994 | Nguyen et al. | 73/37 |
| 5,332,402 | A | | 7/1994 | Teitelbaum | 623/2 |
| 5,370,685 | A | | 12/1994 | Stevens | 623/2 |
| 5,411,552 | A | | 5/1995 | Andersen et al. | 623/2 |
| 5,469,868 | A | | 11/1995 | Reger | 128/898 |
| 5,480,423 | A | | 1/1996 | Ravenscroft et al. | 623/1 |
| 5,500,014 | A | | 3/1996 | Quijano et al. | 623/2 |
| 5,545,214 | A | | 8/1996 | Stevens | 623/2 |
| 5,554,185 | A | | 9/1996 | Block et al. | 623/2 |
| 5,643,208 | A | | 7/1997 | Parodi | 604/96 |
| 5,693,087 | A | | 12/1997 | Parodi | 623/1 |

(Continued)

FOREIGN PATENT DOCUMENTS

EP 0 380 666 8/1990

(Continued)

Primary Examiner—Thomas J Sweet
(74) Attorney, Agent, or Firm—Brooks, Cameron & Huebsch, PLLC

(57) ABSTRACT

Method and apparatus implementing and using techniques for controlling flow in a body lumen, including use of an implantable medical device. The device includes a membrane implantable in a body lumen and invertibly deformable between a first position and a second position. The membrane is invertible in response to the direction of fluid flow through the lumen and can be deformable by fluid flow in the body lumen.

10 Claims, 14 Drawing Sheets

U.S. PATENT DOCUMENTS

| | | | |
|---|---|---|---|
| 5,713,953 A | 2/1998 | Vallana et al. | 623/2 |
| 5,716,370 A | 2/1998 | Williamson, IV et al. | 606/153 |
| 5,735,859 A | 4/1998 | Fischell et al. | 606/108 |
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |
| 6,042,607 A | 3/2000 | Williamson, IV et al. | 623/2 |
| 6,139,575 A | 10/2000 | Shu et al. | 623/2.18 |
| 6,287,334 B1 | 9/2001 | Moll et al. | 623/1.24 |
| 6,312,447 B1 | 11/2001 | Grimes | 606/219 |
| 6,355,030 B1 | 3/2002 | Aldrich et al. | 606/28 |
| 6,402,780 B2 | 6/2002 | Williamson, IV et al. | 623/2.11 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,544,285 B1 * | 4/2003 | Thubrikar et al. | 623/2.12 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,629,534 B1 | 10/2003 | St. Goar, et al. | 128/898 |
| 6,635,085 B1 | 10/2003 | Caffey et al. | 623/2.1 |
| 6,666,885 B2 * | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |

| | | | | | | | |
|---|---|---|---|---|---|---|---|
| 6,964,683 B2 | 11/2005 | Kowalsky et al. | 623/2.36 | 2004/0019378 A1 | 1/2004 | Hlavka et al. | 623/2.11 |
| 6,964,684 B2 | 11/2005 | Ortiz et al. | 623/2.37 | 2004/0024447 A1 | 2/2004 | Haverich | 623/1.24 |
| 6,966,925 B2 | 11/2005 | Stobie | 623/2.11 | 2004/0024451 A1 | 2/2004 | Johnson et al. | 623/2.11 |
| 6,966,926 B2 | 11/2005 | Mathis | 623/2.36 | 2004/0024452 A1 | 2/2004 | Kruse et al. | 623/2.13 |
| 6,974,464 B2 | 12/2005 | Quijano et al. | 606/108 | 2004/0030321 A1 | 2/2004 | Fangrow, Jr. | 604/533 |
| 6,974,474 B2 | 12/2005 | Pavcnik et al. | 623/1.24 | 2004/0030381 A1 | 2/2004 | Shu | 623/2.11 |
| 6,974,476 B2 | 12/2005 | McGuckin, Jr. et al. | 623/2.36 | 2004/0030382 A1 | 2/2004 | St. Goar et al. | 623/2.36 |
| 6,976,995 B2 | 12/2005 | Mathis et al. | 623/2.37 | 2004/0030405 A1 | 2/2004 | Carpentier et al. | 623/23.72 |
| 6,979,350 B2 | 12/2005 | Moll et al. | 623/1.24 | 2004/0034380 A1 | 2/2004 | Woolfson et al. | 606/170 |
| 6,986,775 B2 | 1/2006 | Morales et al. | 606/139 | 2004/0034411 A1 | 2/2004 | Quijano et al. | 623/2.11 |
| 6,989,027 B2 | 1/2006 | Allen et al. | 623/2.18 | 2004/0039436 A1 | 2/2004 | Spenser et al. | 623/1.13 |
| 6,989,028 B2 | 1/2006 | Lashinski et al. | 623/2.37 | 2004/0039442 A1 | 2/2004 | St. Goar et al. | 623/2.36 |
| 6,997,950 B2 | 2/2006 | Chawla | 623/2.1 | 2004/0039443 A1 | 2/2004 | Solem et al. | 623/2.37 |
| 6,997,951 B2 | 2/2006 | Solem et al. | 623/2.37 | 2004/0044350 A1 | 3/2004 | Martin et al. | 606/139 |
| 7,004,176 B2 | 2/2006 | Lau | 128/898 | 2004/0044365 A1 | 3/2004 | Bachman | 606/213 |
| 7,007,396 B2 | 3/2006 | Rudko et al. | 33/512 | 2004/0044403 A1 | 3/2004 | Bischoff et al. | 623/1.41 |
| 7,011,669 B2 | 3/2006 | Kimblad | 606/151 | 2004/0049207 A1 | 3/2004 | Goldfarb et al. | 606/139 |
| 7,011,681 B2 | 3/2006 | Vesely | 623/2.11 | 2004/0049211 A1 | 3/2004 | Tremulis et al. | 606/153 |
| 7,011,682 B2 | 3/2006 | Lahsinski et al. | 623/2.37 | 2004/0049266 A1 | 3/2004 | Anduiza et al. | 623/2.11 |
| 7,018,406 B2 | 3/2006 | Seguin et al. | 623/2.1 | 2004/0059351 A1 | 3/2004 | Eigler et al. | 606/148 |
| 7,018,407 B1 | 3/2006 | Wright et al. | 623/2.11 | 2004/0059411 A1* | 3/2004 | Strecker | 623/1.23 |
| 7,018,408 B2 | 3/2006 | Bailey et al. | 623/2.11 | 2004/0059412 A1 | 3/2004 | Lytle, IV et al. | 623/2.11 |
| 7,022,134 B1 | 4/2006 | Quijano et al. | 623/1.24 | 2004/0060161 A1 | 4/2004 | Leal et al. | 29/558 |
| 7,025,780 B2 | 4/2006 | Gabbay | 623/2.13 | 2004/0073301 A1 | 4/2004 | Donlon et al. | 623/2.11 |
| 7,033,390 B2 | 4/2006 | Johnson et al. | 623/2.11 | 2004/0073302 A1 | 4/2004 | Rourke et al. | 623/2.36 |
| 7,037,333 B2 | 5/2006 | Myers et al. | 623/2.13 | 2004/0078072 A1 | 4/2004 | Tu et al. | 623/1.23 |
| 7,037,334 B1 | 5/2006 | Hlavka et al. | 623/2.36 | 2004/0078074 A1 | 4/2004 | Anderson et al. | 623/2.11 |
| 7,041,128 B2 | 5/2006 | McGuckin, Jr. et al. | 623/1.36 | 2004/0082910 A1 | 4/2004 | Constantz et al. | 604/101.04 |
| 7,041,132 B2 | 5/2006 | Quijano et al. | 623/2.11 | 2004/0082923 A1 | 4/2004 | Field | 604/267 |
| 7,044,966 B2 | 5/2006 | Svanidze et al. | 623/2.1 | 2004/0082991 A1 | 4/2004 | Nguyen et al. | 623/2.14 |
| 7,044,967 B1 | 5/2006 | Solem et al. | 623/2.36 | 2004/0087975 A1 | 5/2004 | Lucatero et al. | 606/139 |
| 7,048,754 B2 | 5/2006 | Martin et al. | 606/232 | 2004/0088045 A1 | 5/2004 | Cox | 623/2.13 |
| 7,048,757 B2 | 5/2006 | Shaknovich | 623/1.24 | 2004/0088046 A1* | 5/2004 | Speziali | 623/2.19 |
| 7,052,487 B2 | 5/2006 | Cohn et al. | 604/509 | 2004/0092858 A1 | 5/2004 | Wilson et al. | 604/9 |
| 7,052,507 B2 | 5/2006 | Wakuda et al. | 606/194 | 2004/0093060 A1 | 5/2004 | Seguin et al. | 623/1.11 |
| 7,063,722 B2 | 6/2006 | Marquez | 623/2.36 | 2004/0093070 A1 | 5/2004 | Hojeibane et al. | 623/1.15 |
| 7,066,954 B2 | 6/2006 | Ryan et al. | 623/2.36 | 2004/0093080 A1 | 5/2004 | Helmus et al. | 623/2.41 |
| 7,070,616 B2 | 7/2006 | Majercak et al. | 623/1.24 | 2004/0097979 A1 | 5/2004 | Svanidze et al. | 606/151 |
| 7,070,618 B2 | 7/2006 | Streeter | 623/2.36 | 2004/0098098 A1 | 5/2004 | McGuckin, Jr. et al. | 623/1.14 |
| 7,077,862 B2 | 7/2006 | Vidlund et al. | 623/2.36 | 2004/0098112 A1 | 5/2004 | DiMatteo et al. | 623/1.24 |
| 7,081,131 B2 | 7/2006 | Thornton | 623/1.24 | 2004/0102839 A1 | 5/2004 | Cohn et al. | 623/2.11 |
| 7,087,064 B1 | 8/2006 | Hyde | 606/142 | 2004/0102840 A1 | 5/2004 | Solem et al. | 623/2.11 |
| 7,089,051 B2 | 8/2006 | Jäverud et al. | 600/547 | 2004/0102842 A1 | 5/2004 | Jansen | 623/2.38 |
| 7,090,695 B2 | 8/2006 | Solem et al. | 623/2.37 | 2004/0106976 A1 | 6/2004 | Bailey et al. | 623/1.11 |
| 2002/0013571 A1 | 1/2002 | Goldfarb et al. | 606/1 | 2004/0106990 A1 | 6/2004 | Spence et al. | 623/2.11 |
| 2002/0026216 A1 | 2/2002 | Grimes | 606/213 | 2004/0106991 A1 | 6/2004 | Hopkins et al. | 623/2.13 |
| 2002/0052651 A1* | 5/2002 | Myers et al. | 623/2.15 | 2004/0111096 A1 | 6/2004 | Tu et al. | 606/108 |
| 2002/0072794 A1* | 6/2002 | Gabbay | 623/2.12 | 2004/0117009 A1 | 6/2004 | Cali et al. | 623/2.12 |
| 2002/0082630 A1 | 6/2002 | Menz et al. | 606/167 | 2004/0122448 A1 | 6/2004 | Levine | 606/139 |
| 2002/0123802 A1 | 9/2002 | Snyders | 623/2.18 | 2004/0122512 A1 | 6/2004 | Navia et al. | 623/2.12 |
| 2002/0151970 A1 | 10/2002 | Garrison et al. | 623/2.11 | 2004/0122513 A1 | 6/2004 | Navia et al. | 623/2.12 |
| 2002/0183835 A1 | 12/2002 | Taylor et al. | 623/2.11 | 2004/0122514 A1 | 6/2004 | Fogarty et al. | 623/2.14 |
| 2002/0183838 A1 | 12/2002 | Liddicoat et al. | 623/2.11 | 2004/0122515 A1 | 6/2004 | Chu | 623/2.29 |
| 2002/0198594 A1 | 12/2002 | Schreck | 623/2.11 | 2004/0122516 A1 | 6/2004 | Fogarty et al. | 623/2.37 |
| 2003/0050694 A1 | 3/2003 | Yang et al. | 623/2.11 | 2004/0127979 A1 | 7/2004 | Wilson et al. | 623/2.1 |
| 2003/0130729 A1 | 7/2003 | Paniagua et al. | 623/2.11 | 2004/0127980 A1 | 7/2004 | Kowalsky et al. | 623/2.11 |
| 2003/0163194 A1 | 8/2003 | Quijano et al. | 623/2.11 | 2004/0127981 A1 | 7/2004 | Rahdert et al. | 623/2.36 |
| 2003/0167071 A1 | 9/2003 | Martin et al. | 606/232 | 2004/0127982 A1 | 7/2004 | Machold et al. | 623/2.36 |
| 2003/0171806 A1 | 9/2003 | Mathis et al. | 623/2.36 | 2004/0133220 A1 | 7/2004 | Lashinski et al. | 606/151 |
| 2003/0199975 A1 | 10/2003 | Gabbay | 623/2.36 | 2004/0133267 A1 | 7/2004 | Lane | 623/1.24 |
| 2003/0229394 A1 | 12/2003 | Ogle et al. | 623/2.14 | 2004/0133273 A1 | 7/2004 | Cox | 623/2.11 |
| 2003/0229395 A1 | 12/2003 | Cox | 623/2.36 | 2004/0138742 A1 | 7/2004 | Myers et al. | 623/2.12 |
| 2003/0233142 A1 | 12/2003 | Morales et al. | 623/2.37 | 2004/0138743 A1 | 7/2004 | Myers et al. | 623/2.13 |
| 2003/0236568 A1 | 12/2003 | Hojeibane et al. | 623/1.24 | 2004/0138744 A1 | 7/2004 | Lashinski et al. | 623/2.36 |
| 2003/0236569 A1 | 12/2003 | Mathis et al. | 623/1.26 | 2004/0138745 A1 | 7/2004 | Macoviak et al. | 623/2.36 |
| 2004/0002719 A1 | 1/2004 | Oz et al. | 606/142 | 2004/0148018 A1 | 7/2004 | Carpentier et al. | 623/2.18 |
| 2004/0003819 A1 | 1/2004 | St. Goar et al. | 128/898 | 2004/0148019 A1 | 7/2004 | Vidlund et al. | 623/2.36 |
| 2004/0010305 A1 | 1/2004 | Alferness et al. | 623/1.11 | 2004/0148020 A1 | 7/2004 | Vidlund et al. | 623/2.36 |
| 2004/0015230 A1 | 1/2004 | Moll et al. | 623/1.24 | 2004/0153052 A1 | 8/2004 | Mathis | 606/1 |
| 2004/0015232 A1 | 1/2004 | Shu et al. | 623/2.4 | 2004/0153146 A1 | 8/2004 | Lashinski et al. | 623/2.36 |
| 2004/0015233 A1 | 1/2004 | Jansen | 623/2.18 | 2004/0153147 A1 | 8/2004 | Mathis | 623/2.37 |
| 2004/0019374 A1 | 1/2004 | Hojeibane et al. | 623/1.13 | 2004/0158321 A1 | 8/2004 | Reuter et al. | 623/2.36 |
| 2004/0019377 A1 | 1/2004 | Taylor et al. | 623/2.11 | 2004/0162610 A1 | 8/2004 | Liska et al. | 623/2.11 |

| | | | | | | | |
|---|---|---|---|---|---|---|---|
| 2004/0167539 A1 | 8/2004 | Kuehn et al. | 606/108 | 2005/0038506 A1 | 2/2005 | Webler et al. | 623/2.11 |
| 2004/0167620 A1 | 8/2004 | Ortiz et al. | 623/2.11 | 2005/0038507 A1 | 2/2005 | Alferness et al. | 623/2.11 |
| 2004/0172046 A1 | 9/2004 | Hlavka et al. | 606/142 | 2005/0043790 A1 | 2/2005 | Seguin | 623/2.18 |
| 2004/0176839 A1 | 9/2004 | Huynh et al. | 623/2.4 | 2005/0043792 A1 | 2/2005 | Solem et al. | 623/2.36 |
| 2004/0176840 A1 | 9/2004 | Langberg et al. | 623/2.37 | 2005/0049679 A1 | 3/2005 | Taylor et al. | 623/1.15 |
| 2004/0181238 A1 | 9/2004 | Zarbatany et al. | 606/108 | 2005/0049692 A1 | 3/2005 | Numamoto et al. | 623/1.24 |
| 2004/0186444 A1 | 9/2004 | Daly et al. | 604/247 | 2005/0049696 A1 | 3/2005 | Siess et al. | 623/2.11 |
| 2004/0186558 A1 | 9/2004 | Pavcnik et al. | 623/1.24 | 2005/0049697 A1 | 3/2005 | Sievers | 623/2.26 |
| 2004/0186561 A1 | 9/2004 | McGuckin, Jr. et al. | 623/1.36 | 2005/0054977 A1 | 3/2005 | Laird et al. | 604/96.01 |
| 2004/0186563 A1 | 9/2004 | Lobbi | 623/2.11 | 2005/0055079 A1 | 3/2005 | Duran | 623/1.13 |
| 2004/0186565 A1 | 9/2004 | Schreck | 623/2.18 | 2005/0055087 A1 | 3/2005 | Starksen | 623/2.11 |
| 2004/0186566 A1 | 9/2004 | Hindrichs et al. | 623/2.37 | 2005/0055088 A1 | 3/2005 | Liddicoat et al. | 623/2.11 |
| 2004/0193191 A1 | 9/2004 | Starksen et al. | 606/153 | 2005/0055089 A1 | 3/2005 | Macoviak et al. | 623/2.37 |
| 2004/0193253 A1 | 9/2004 | Thorpe et al. | 623/1.24 | 2005/0060029 A1 | 3/2005 | Le et al. | 623/2.11 |
| 2004/0193260 A1 | 9/2004 | Alferness et al. | 623/2.11 | 2005/0060030 A1 | 3/2005 | Lashinski et al. | 623/2.37 |
| 2004/0199155 A1 | 10/2004 | Mollenauer | 606/27 | 2005/0065460 A1 | 3/2005 | Laird | 604/20 |
| 2004/0199183 A1 | 10/2004 | Oz et al. | 606/142 | 2005/0065550 A1 | 3/2005 | Starksen et al. | 606/219 |
| 2004/0199191 A1 | 10/2004 | Schwartz | 606/159 | 2005/0065594 A1 | 3/2005 | DiMatteo et al. | 623/1.24 |
| 2004/0204758 A1 | 10/2004 | Eberhardt et al. | 623/2.15 | 2005/0065597 A1 | 3/2005 | Lansac | 623/2.11 |
| 2004/0206363 A1 | 10/2004 | McCarthy et al. | 128/898 | 2005/0070998 A1 | 3/2005 | Rourke et al. | 623/2.11 |
| 2004/0210240 A1 | 10/2004 | Saint | 606/139 | 2005/0075584 A1 | 4/2005 | Cali | 600/587 |
| 2004/0210301 A1 | 10/2004 | Obermiller | 623/1.24 | 2005/0075659 A1 | 4/2005 | Realyvasquez et al. | 606/167 |
| 2004/0210303 A1 | 10/2004 | Sedransk | 623/2.1 | 2005/0075662 A1 | 4/2005 | Pedersen et al. | 606/194 |
| 2004/0210304 A1 | 10/2004 | Seguin et al. | 623/2.11 | 2005/0075712 A1 | 4/2005 | Biancucci et al. | 623/1.11 |
| 2004/0210305 A1 | 10/2004 | Shu et al. | 623/2.11 | 2005/0075713 A1 | 4/2005 | Biancucci et al. | 623/1.11 |
| 2004/0210306 A1 | 10/2004 | Quijano et al. | 623/2.17 | 2005/0075717 A1 | 4/2005 | Nguyen et al. | 623/1.26 |
| 2004/0210307 A1 | 10/2004 | Khairkhahan | 623/2.18 | 2005/0075718 A1 | 4/2005 | Nguyen et al. | 623/1.26 |
| 2004/0215333 A1 | 10/2004 | Duran et al. | 623/1.24 | 2005/0075719 A1 | 4/2005 | Bergheim | 623/1.26 |
| 2004/0215339 A1 | 10/2004 | Drasler et al. | 623/3.1 | 2005/0075720 A1 | 4/2005 | Nguyen et al. | 623/1.26 |
| 2004/0220654 A1 | 11/2004 | Mathis et al. | 623/1.11 | 2005/0075723 A1 | 4/2005 | Schroeder et al. | 623/2.1 |
| 2004/0220657 A1 | 11/2004 | Nieminen et al. | 623/1.15 | 2005/0075724 A1 | 4/2005 | Svanidze et al. | 623/2.11 |
| 2004/0225322 A1 | 11/2004 | Garrison et al. | 606/200 | 2005/0075725 A1 | 4/2005 | Rowe | 623/2.14 |
| 2004/0225344 A1 | 11/2004 | Hoffa et al. | 623/1.1 | 2005/0075726 A1 | 4/2005 | Svanidze et al. | 623/2.14 |
| 2004/0225348 A1 | 11/2004 | Case et al. | 623/1.15 | 2005/0075729 A1 | 4/2005 | Nguyen et al. | 623/2.18 |
| 2004/0225352 A1 | 11/2004 | Osborne et al. | 623/1.24 | 2005/0075730 A1 | 4/2005 | Myers et al. | 623/2.18 |
| 2004/0225353 A1 | 11/2004 | McGuckin, Jr. et al. | 623/2.11 | 2005/0075731 A1 | 4/2005 | Artof et al. | 623/2.18 |
| 2004/0225354 A1 | 11/2004 | Allen et al. | 623/2.11 | 2005/0080483 A1 | 4/2005 | Solem et al. | 623/2.11 |
| 2004/0225355 A1 | 11/2004 | Stevens | 623/2.11 | 2005/0085900 A1 | 4/2005 | Case et al. | 623/1.24 |
| 2004/0225356 A1 | 11/2004 | Frater | 623/2.14 | 2005/0085903 A1 | 4/2005 | Lau | 623/2.11 |
| 2004/0230117 A1 | 11/2004 | Tosaya et al. | 600/439 | 2005/0085904 A1 | 4/2005 | Lemmon | 623/2.11 |
| 2004/0230297 A1 | 11/2004 | Thornton | 623/1.24 | 2005/0090846 A1 | 4/2005 | Pedersen et al. | 606/159 |
| 2004/0236411 A1 | 11/2004 | Sarac et al. | 623/1.26 | 2005/0096735 A1 | 5/2005 | Hojeibane et al. | 623/1.24 |
| 2004/0236418 A1 | 11/2004 | Stevens | 623/2.11 | 2005/0096738 A1 | 5/2005 | Cali et al. | 623/2.18 |
| 2004/0236419 A1 | 11/2004 | Milo | 623/2.36 | 2005/0096739 A1 | 5/2005 | Cao | 623/2.19 |
| 2004/0243153 A1 | 12/2004 | Liddicoat et al. | 606/151 | 2005/0096740 A1 | 5/2005 | Langberg et al. | 623/2.36 |
| 2004/0243219 A1 | 12/2004 | Fischer et al. | 623/1.15 | 2005/0101975 A1 | 5/2005 | Nguyen et al. | 606/151 |
| 2004/0243227 A1 | 12/2004 | Starksen et al. | 623/2.11 | 2005/0102026 A1 | 5/2005 | Turner et al. | 623/2.1 |
| 2004/0243228 A1 | 12/2004 | Kowalsky et al. | 623/2.11 | 2005/0107810 A1 | 5/2005 | Morales et al. | 606/143 |
| 2004/0243230 A1 | 12/2004 | Navia et al. | 623/2.36 | 2005/0107811 A1 | 5/2005 | Starksen et al. | 606/143 |
| 2004/0254600 A1 | 12/2004 | Zarbatany et al. | 606/194 | 2005/0107812 A1 | 5/2005 | Starksen et al. | 606/143 |
| 2004/0254636 A1 | 12/2004 | Flagle et al. | 623/1.24 | 2005/0107872 A1 | 5/2005 | Mensah et al. | 623/2.14 |
| 2004/0260276 A1 | 12/2004 | Rudko et al. | 606/15 | 2005/0113910 A1 | 5/2005 | Paniagua et al. | 623/2.14 |
| 2004/0260317 A1 | 12/2004 | Bloom et al. | 606/151 | 2005/0119673 A1 | 6/2005 | Gordon et al. | 606/151 |
| 2004/0260322 A1 | 12/2004 | Rudko et al. | 606/167 | 2005/0119734 A1 | 6/2005 | Spence et al. | 623/2.11 |
| 2004/0260389 A1 | 12/2004 | Case et al. | 623/1.24 | 2005/0119735 A1 | 6/2005 | Spence et al. | 623/2.36 |
| 2004/0260390 A1 | 12/2004 | Sarac et al. | 623/1.24 | 2005/0125011 A1 | 6/2005 | Spence et al. | 606/144 |
| 2004/0260393 A1 | 12/2004 | Rahdert et al. | 623/2.36 | 2005/0131438 A1 | 6/2005 | Cohn | 606/170 |
| 2004/0260394 A1 | 12/2004 | Douk et al. | 623/2.36 | 2005/0137449 A1 | 6/2005 | Nieminen et al. | 600/37 |
| 2004/0267357 A1 | 12/2004 | Allen et al. | 623/2.11 | 2005/0137450 A1 | 6/2005 | Aronson et al. | 600/37 |
| 2005/0004583 A1 | 1/2005 | Oz et al. | 606/142 | 2005/0137451 A1 | 6/2005 | Gordon et al. | 600/37 |
| 2005/0004667 A1 | 1/2005 | Swinford et al. | 623/2.36 | 2005/0137676 A1 | 6/2005 | Richardson et al. | 623/1.11 |
| 2005/0010285 A1 | 1/2005 | Lambrecht et al. | 623/2.18 | 2005/0137681 A1 | 6/2005 | Shoemaker et al. | 623/1.23 |
| 2005/0010287 A1 | 1/2005 | Macoviak et al. | 623/2.36 | 2005/0137682 A1 | 6/2005 | Justino | 623/1.24 |
| 2005/0015112 A1 | 1/2005 | Cohn et al. | 606/200 | 2005/0137685 A1 | 6/2005 | Nieminen et al. | 623/2.11 |
| 2005/0021056 A1 | 1/2005 | St. Goar et al. | 606/144 | 2005/0137686 A1 | 6/2005 | Salahieh et al. | 623/2.11 |
| 2005/0021136 A1 | 1/2005 | Xie et al. | 623/2.14 | 2005/0137688 A1 | 6/2005 | Salahieh et al. | 623/2.11 |
| 2005/0027261 A1 | 2/2005 | Weaver et al. | 604/246 | 2005/0137689 A1 | 6/2005 | Salahieh et al. | 623/2.11 |
| 2005/0027348 A1 | 2/2005 | Case et al. | 623/1.24 | 2005/0137690 A1 | 6/2005 | Salahieh et al. | 623/2.11 |
| 2005/0027351 A1 | 2/2005 | Reuter et al. | 623/2.11 | 2005/0137691 A1 | 6/2005 | Salahieh et al. | 623/2.11 |
| 2005/0027353 A1 | 2/2005 | Alferness et al. | 623/2.11 | 2005/0137692 A1 | 6/2005 | Haug et al. | 623/2.11 |
| 2005/0033398 A1 | 2/2005 | Seguin | 623/1.11 | 2005/0137693 A1 | 6/2005 | Haug et al. | 623/2.11 |
| 2005/0033419 A1 | 2/2005 | Alferness et al. | 623/2.11 | 2005/0137694 A1 | 6/2005 | Haug et al. | 623/2.11 |
| 2005/0033446 A1 | 2/2005 | Deem et al. | 623/23.6 | 2005/0137696 A1 | 6/2005 | Salahieh et al. | 623/2.11 |

| Pub. No. | Date | Inventor | Class |
|---|---|---|---|
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Starksen et al. | 604/510 |
| 2006/0025784 A1 | 2/2006 | Starksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson et al. | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |

| Pub. No. | Date | Inventor | Class |
|---|---|---|---|
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2004/082537 | 9/2004 |
| WO | WO 2004/082538 | 9/2004 |
| WO | WO 2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/021063 | 3/2005 |
| WO | WO 2005/023155 | 3/2005 |
| WO | WO 2005/025644 | 3/2005 |
| WO | WO 2005/027790 | 3/2005 |
| WO | WO 2005/027797 | 3/2005 |
| WO | WO 2005/034812 | 4/2005 |
| WO | WO 2005/039428 | 5/2005 |
| WO | WO 2005/039452 | 5/2005 |
| WO | WO 2005/046488 | 5/2005 |
| WO | WO 2005/046528 | 5/2005 |
| WO | WO 2005/046529 | 5/2005 |
| WO | WO 2005/046530 | 5/2005 |
| WO | WO 2005/046531 | 5/2005 |
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |
| WO | WO 2005/084595 | 9/2005 |
| WO | WO 2005/087139 | 9/2005 |
| WO | WO 2005/087140 | 9/2005 |

| | | | | | | |
|---|---|---|---|---|---|---|
| WO | WO 2006/000763 | 1/2006 | | WO | WO 2006/035415 | 4/2006 |
| WO | WO 2006/000776 | 1/2006 | | WO | WO 2006/041505 | 4/2006 |
| WO | WO 2006/002492 | 1/2006 | | WO | WO 2006/044679 | 4/2006 |
| WO | WO 2006/004679 | 1/2006 | | WO | WO 2006/048664 | 5/2006 |
| WO | WO 2006/005015 | 1/2006 | | WO | WO 2006/050459 | 5/2006 |
| WO | WO 2006/009690 | 1/2006 | | WO | WO 2006/050460 | 5/2006 |
| WO | WO 2006/011127 | 2/2006 | | WO | WO 2006/054107 | 5/2006 |
| WO | WO 2006/012011 | 2/2006 | | WO | WO 2006/054930 | 5/2006 |
| WO | WO 2006/012013 | 2/2006 | | WO | WO 2006/055982 | 5/2006 |
| WO | WO 2006/012038 | 2/2006 | | WO | WO 2006/060546 | 6/2006 |
| WO | WO 2006/012068 | 2/2006 | | WO | WO 2006/063108 | 6/2006 |
| WO | WO 2006/012322 | 2/2006 | | WO | WO 2006/063181 | 6/2006 |
| WO | WO 2006/019498 | 2/2006 | | WO | WO 2006/063199 | 6/2006 |
| WO | WO 2006/026371 | 3/2006 | | WO | WO 2006/064490 | 6/2006 |
| WO | WO 2006/026377 | 3/2006 | | WO | WO 2006/065212 | 6/2006 |
| WO | WO 2006/026912 | 3/2006 | | WO | WO 2006/065930 | 6/2006 |
| WO | WO 2006/027499 | 3/2006 | | WO | WO 2006/066148 | 6/2006 |
| WO | WO 2006/028821 | 3/2006 | | WO | WO 2006/066150 | 6/2006 |
| WO | WO 2006/029062 | 3/2006 | | WO | WO 2006/069094 | 6/2006 |
| WO | WO 2006/031436 | 3/2006 | | WO | WO 2006/070372 | 7/2006 |
| WO | WO 2006/031469 | 3/2006 | | WO | WO 2006/073628 | 7/2006 |
| WO | WO 2006/032051 | 3/2006 | | WO | WO 2006/076890 | 7/2006 |
| WO | WO 2006/034245 | 3/2006 | | | | |

* cited by examiner

ARTIFICIAL VALVE

CROSS-REFERENCE TO RELATED APPLICATIONS

This application is a continuation of U.S. application Ser. No. 10/873,052, filed Jun. 22, 2004, now U.S. Pat. No. 7,081,131 issued Jul. 25, 2006, which is a continuation of U.S. application Ser. No. 10/115,557, filed Apr. 3, 2002, now U.S. Pat. No. 6,752,828 issued Jun. 22, 2004, the specifications of which are incorporated herein by reference.

FIELD OF THE INVENTION

This invention relates to medical devices for use in a body lumen.

BACKGROUND

A venous valve functions to prevent retrograde flow of blood and allow only antegrade flow of blood to the heart. Referring to FIG. 1A, a healthy venous valve 12 is illustrated in a vessel 10. The valve is bicuspid, with opposed cusps 14. In the closed condition, the cusps 14 are drawn together to prevent retrograde flow (arrow 16) of blood. Referring to FIG. 1B, if the valve is incompetent, the cusps 14 do not seal properly and retrograde flow of blood occurs. Incompetence of a venous valve is thought to arise from at least the following two medical conditions: varicose veins and chronic venous insufficiency.

SUMMARY

This invention relates to medical devices for use with a body lumen. In one aspect, the invention features a medical device including a membrane implantable in a body lumen and invertibly deformable between a first position and a second position. The membrane is invertible in response to the direction of fluid flow through the lumen and can be deformable by fluid flow in the body lumen. The membrane can be invertible relative to a radial direction of the body lumen. The membrane can be reversibly deformable between the first position and the second position.

Implementations can include one or more of the following. The membrane can define a portion of a cone, and can include an anchoring element adjacent a vertex of the cone. The membrane can include an anchoring element configured to embed within the body lumen, or alternatively configured to penetrate through the body lumen. The anchoring element may be, for example, a loop or a barb. The membrane can be formed of a polymer, for example, a polyurethane, polyethylene or fluoroplastic.

In another aspect, the invention features a medical system. The system includes multiple membranes, each membrane implantable in a body lumen and invertibly deformable between a first position and a second position. Each membrane is invertible in response to the direction of fluid flow through the lumen.

Implementations of the system can include one or more of the following. The membranes can be symmetrically implantable in the body lumen. Each membrane can be invertible relative to a radial direction of the body lumen and can be deformable by fluid flow in the body lumen. At least one membrane can be reversibly deformable between the first position and the second position. At least one membrane can define a portion of a cone and can include an anchoring element adjacent a vertex of the cone. At least one membrane can include an anchoring element configured to embed within the body lumen or alternatively configured to penetrate through the body lumen. The anchoring element can be, for example, a loop or a barb. At least one membrane can be formed of a polymer, for example, a polyurethane, polyethylene or fluoroplastic.

In another aspect, the invention features a method. The method includes positioning at least one membrane in a body lumen, each membrane invertibly deformable between a first position and a second position. Each membrane is invertible in response to the direction of fluid flow through the lumen.

Implementations of the method can include one or more of the following. The method can include positioning multiple membranes in the body lumen. The multiple membranes can be positioned symmetrically in the body lumen. The method can include penetrating an anchoring element of the at least one membrane through the body lumen or, alternatively, embedding an anchoring element of the at least one membrane into the body lumen.

In another aspect, the invention features a method of controlling flow in a body lumen. The method includes invertibly deforming a membrane between a first position and a second position, the membrane being invertible in response to the direction of fluid flow through the lumen. Implementations can include one or more of the following. The membrane in the second position and a portion of the body lumen can define a cavity. Deformation of the membrane can be relative to a radial axis of the body lumen. The membrane can be deformable by fluid flow in the body lumen. The membrane in the first position and the membrane in the second position can be approximately mirror images of each other. The method can further include invertibly deforming a plurality of membranes.

Embodiments may have one or more of the following advantages. One or more invertible membranes, which can function as artificial valve cusps, can be implanted at a treatment site using a catheter. As such, implantation is minimally invasive and avoids surgery and the possibility of the inherent complications. The membrane is fabricated from a polymer such as a polyurethane, polyethylene or fluoroplastic, which materials are more easily accessible than a natural tissue excised from an animal, and can be manufactured with consistency and efficiency that could be more difficult or more expensive using a natural tissue.

Other features, objects, and advantages of the invention will be apparent from the description and drawings, and from the claims.

DETAILED DESCRIPTION

Figure 1A:
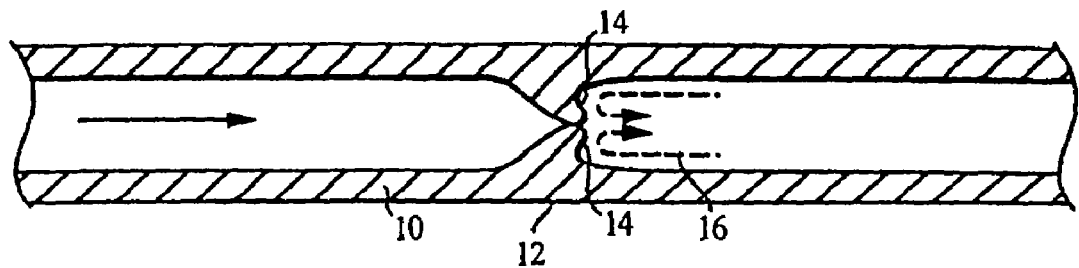
FIGS. 1A and 1B are illustrations of a venous valve and an incompetent venous valve, respectively.
Figure 1B:
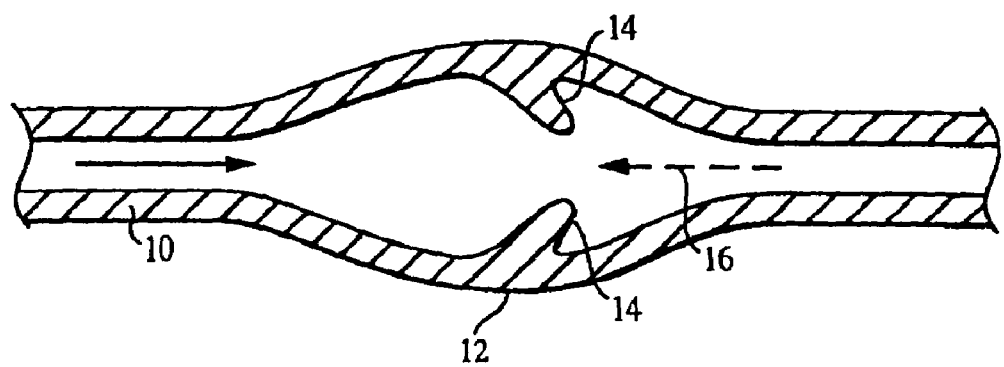

Referring to FIGS. 2A-2C through FIG. 4, a pair of artificial valve cusps 30 are illustrated positioned within a vessel 46, e.g., a vein. Cusps 30 can be positioned upstream or downstream relative to an incompetent venous valve, such as the valve shown in FIG. 1B. Each artificial valve cusp 30 includes at least one anchoring element 38 attached to an invertible portion 42, here, an approximately triangular, flexible membrane. Anchoring element 38 is generally configured to hold invertible portion 39 at a desired location in vessel 46. For example, anchoring element 38 can embed itself within a wall 44 of vessel 46, or penetrate through the wall to secure cusp 30 to the vessel. Invertible portion 42 is capable of deforming between a first position and a second position, e.g., between an opened condition and a closed position, in response to flow of body fluid in vessel 46 to allow or to reduce the flow in the vessel.

Figure 2C:
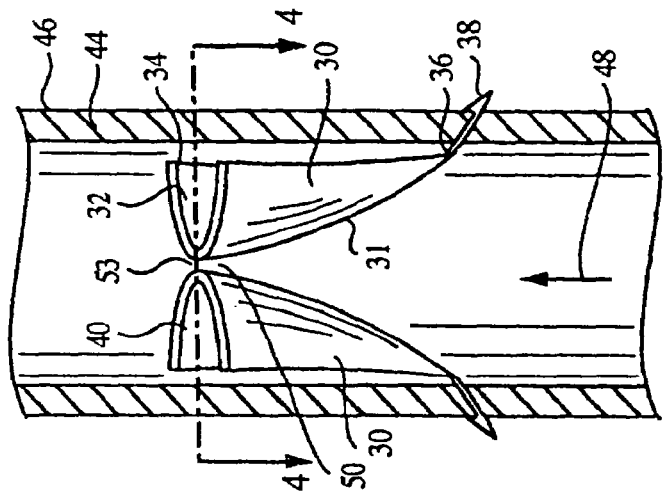
FIGS. 2A, 2B, and 2C are partial perspective views of an embodiment of a valve cusp.
Figure 2B:
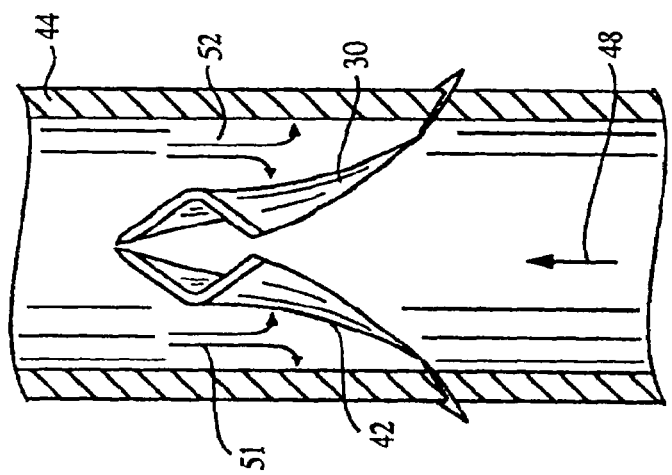
Figure 2A:
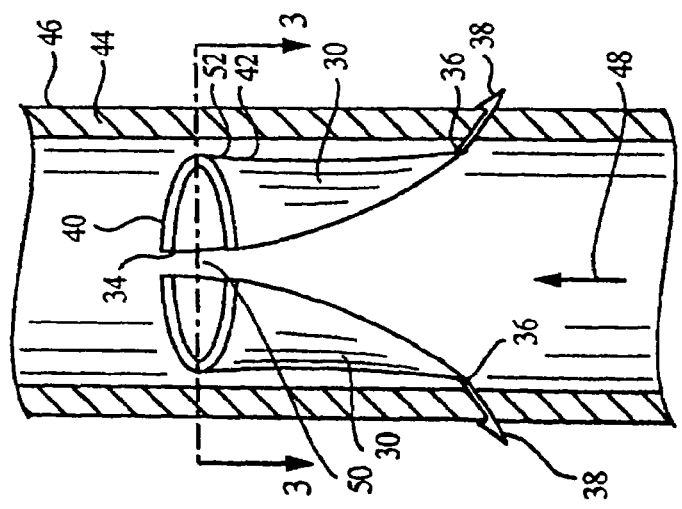
Figure 3:
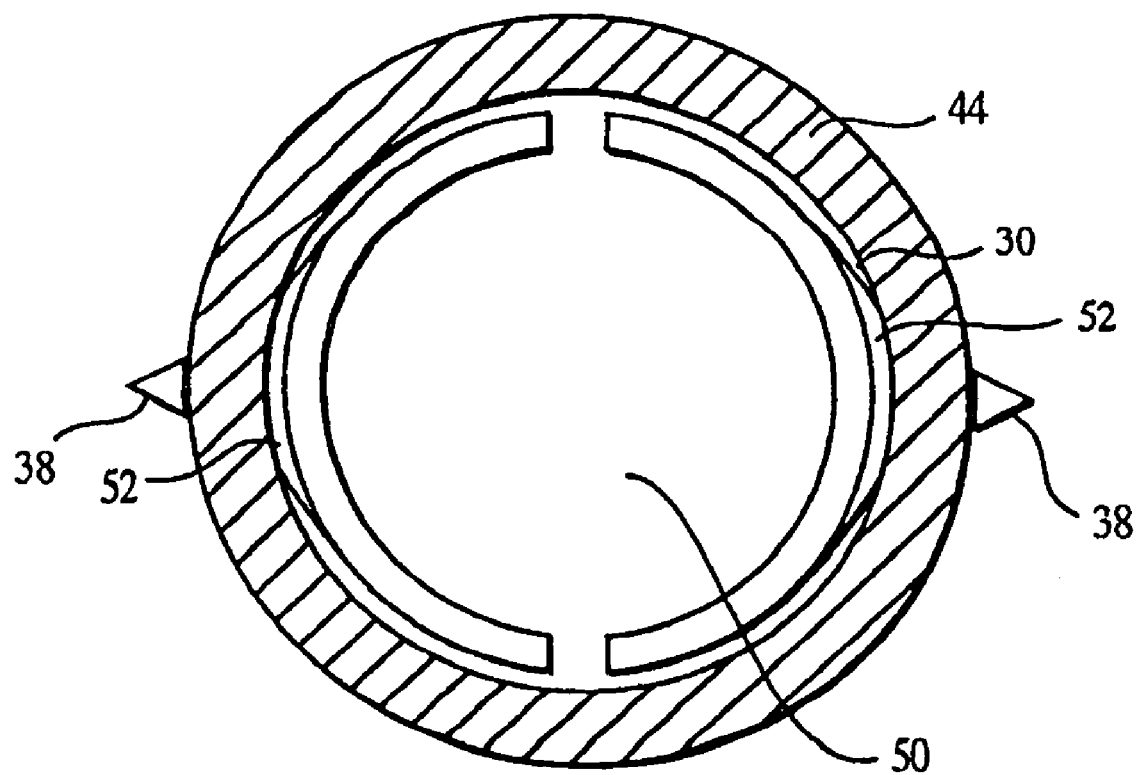
FIG. 3 is a cross-sectional view of the valve cusp of FIG. 2A, taken along line 3-3.

Referring particularly to FIG. 2A and FIG. 3, the cusps 30 are shown in a first position in which each cusp 30 forms an approximate semi-cone, such that an opening 50 is formed by the curved surfaces of the cusps 30. The opening 50 allows antegrade flow of a fluid through the vessel in the direction indicated by arrow 48. The membranes of invertible portions 42 are relatively thin and can conform closely to the vessel wall 44 to maximize the size of opening 50. However, each cusp 30 is also held slightly away from the wall 44 of the vessel 46 by the anchoring element 38, such that a gap 52 is formed between the invertible portion 42 and the wall 44.

Figure 4:
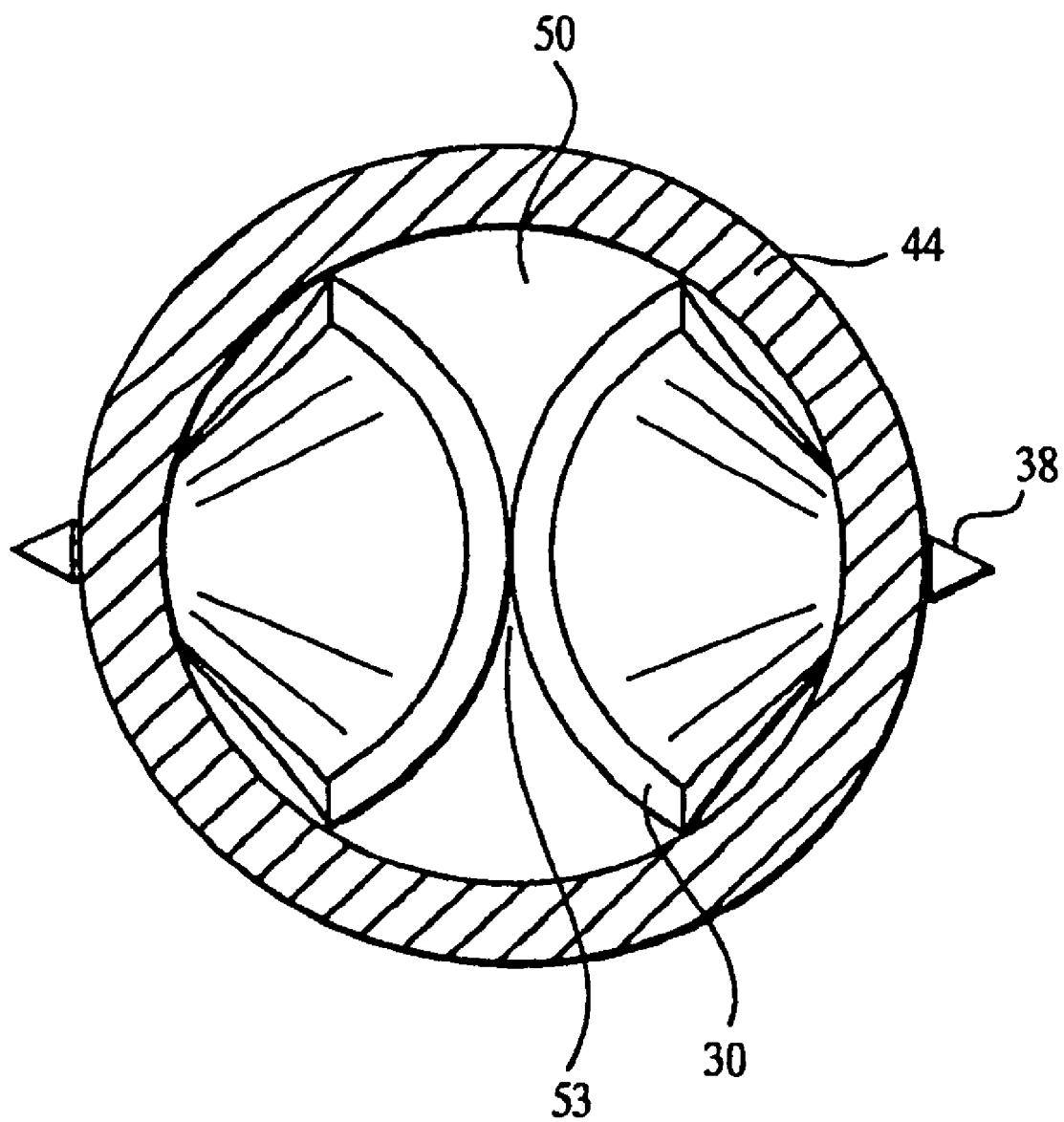
FIG. 4 is a cross-sectional view of the valve cusp of FIG. 2C, taken along line 4-4.

Referring particularly to FIG. 2B, retrograde flow of fluid (arrows 5 1) in the vessel can accumulate in the gap 52 and exert pressure on the invertible portion 42 of the cusp 30. Since invertible portion 42 is flexible, it can deform under the exerted pressure and invert to form another approximate semi-cone, as shown in FIG. 2C. That is, each cusp 30 forming a first semi-cone in the first position can invert or flip relative to a radial axis of vessel 46 to form a second semi-cone that is approximately the mirror image of the first semi-cone. As the interior 32 of the second semi-cone accumulates retrograde flowing fluid, pressure is exerted on the interior of cusp 30, causing the cusp to move away from the wall 44 of the vessel. As a result, the space 53 between the two cusps 30 narrows, the size of opening 50 decreases, and fluid flow through the vessel and past the cusps is reduced (FIG. 4).

The cusps 30 can remain in the second position until antegrade fluid flow exerts sufficient pressure on the surface of cusps 30 opposite interior 32 and inverts the cusps to the first position. Thus, cusps 30 provide an artificial valve that automatically responds to the flow of fluid or pressure changes in vessel 46.

Figure 5A:
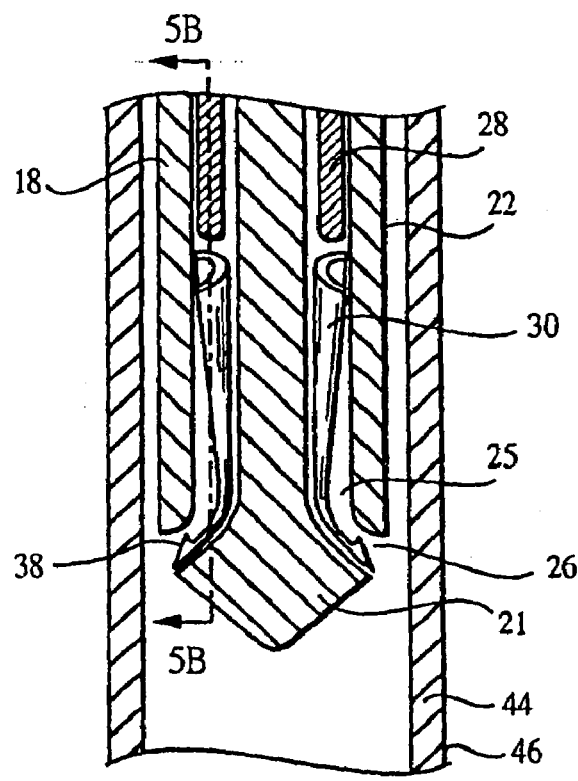
FIGS. 5A, 5B, 5C, 5D and 5E are schematic views of an embodiment of a method for implanting a valve cusp.
Figure 5B:
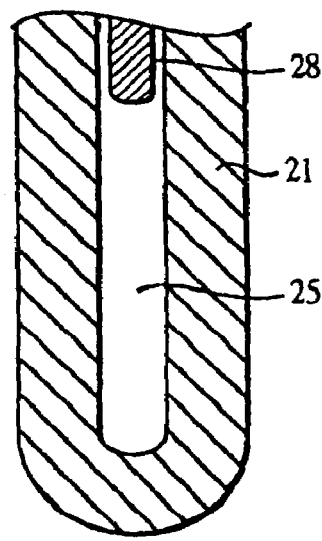

FIGS. 5A to 5E show one method of positioning cusps 30 at a treatment site in vessel 46 using a catheter 18 that may be delivered into the vessel 46 ercutaneously. The catheter 18 is generally adapted for delivery through the vessel 46, e.g., using a guidewire. Catheter 18 includes a long, flexible body having a central portion 21, and a retractable sheath 22 over the central portion. Referring particularly to FIG. 5B, a cross-sectional view of FIG. 5A taken along line 5-5, two grooves 25 are formed on either side of the central portion 21, and a push rod 28 is positioned inside each of the grooves 25. Each cusp 30 is positioned in a groove 25 in a compacted state and held in place by the retractable sheath 22 until delivery at the treatment site.

Figure 5C:
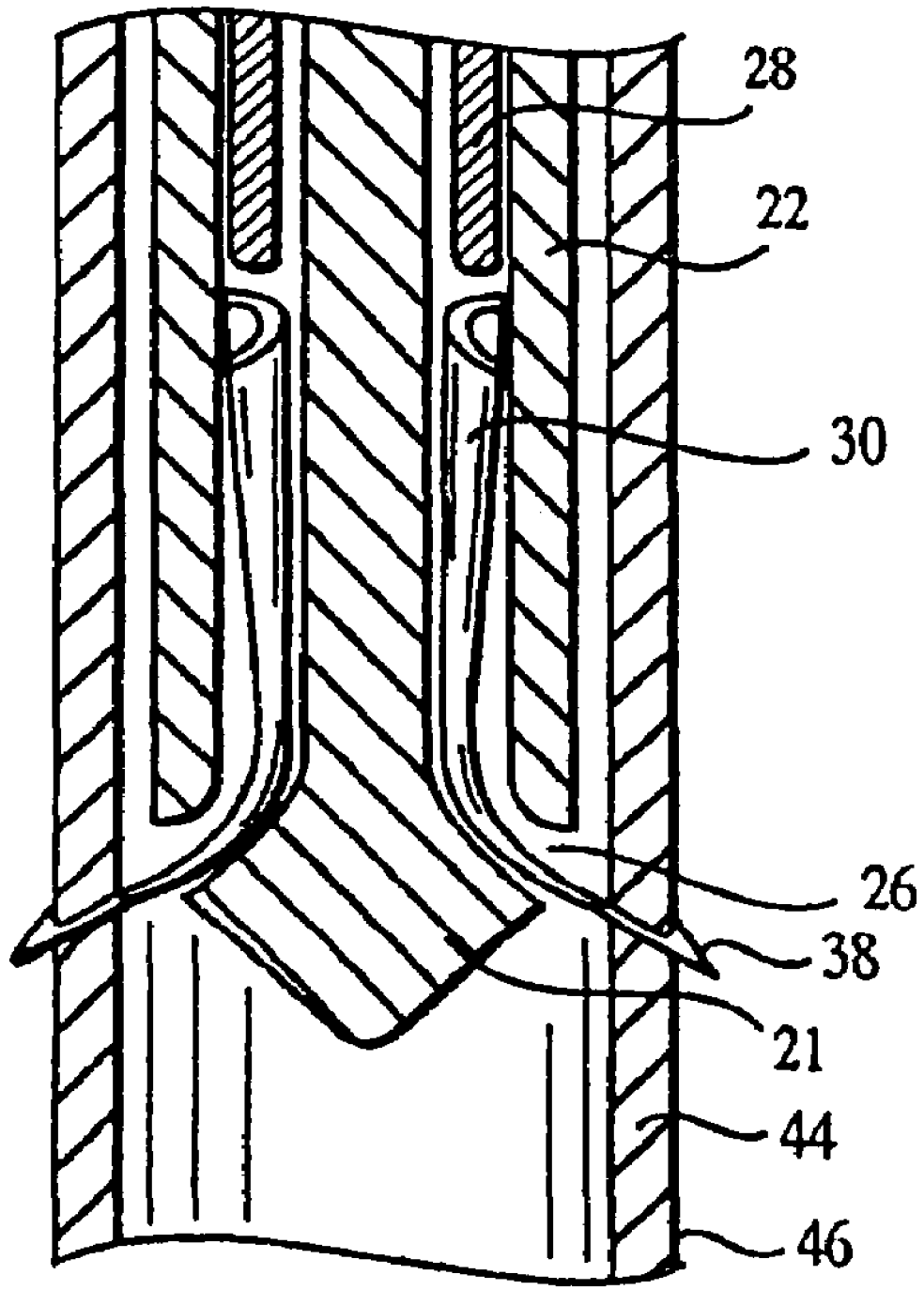

Catheter 18 can be delivered to the treatment site using endoprosthesis delivery techniques, e.g., by tracking an emplaced guidewire with central lumen 101. At the treatment site, the retractable sheath 22 is retracted proximally to form an opening 26 at the end of each groove 25. Referring particularly to FIG. 5C, push rods 28 are used to push each cusp distally toward the opening 26 to push the anchoring element 38 out of the opening 26. The cusps 30 are pushed out of the openings 26 until the anchoring elements 38 secure the cusps 30 to the wall 44 of the vessel 46. For example, the anchoring elements 38 can embed within the wall 44 or penetrate the wall 44 and secure to the exterior of the vessel 46.

Figure 5D:
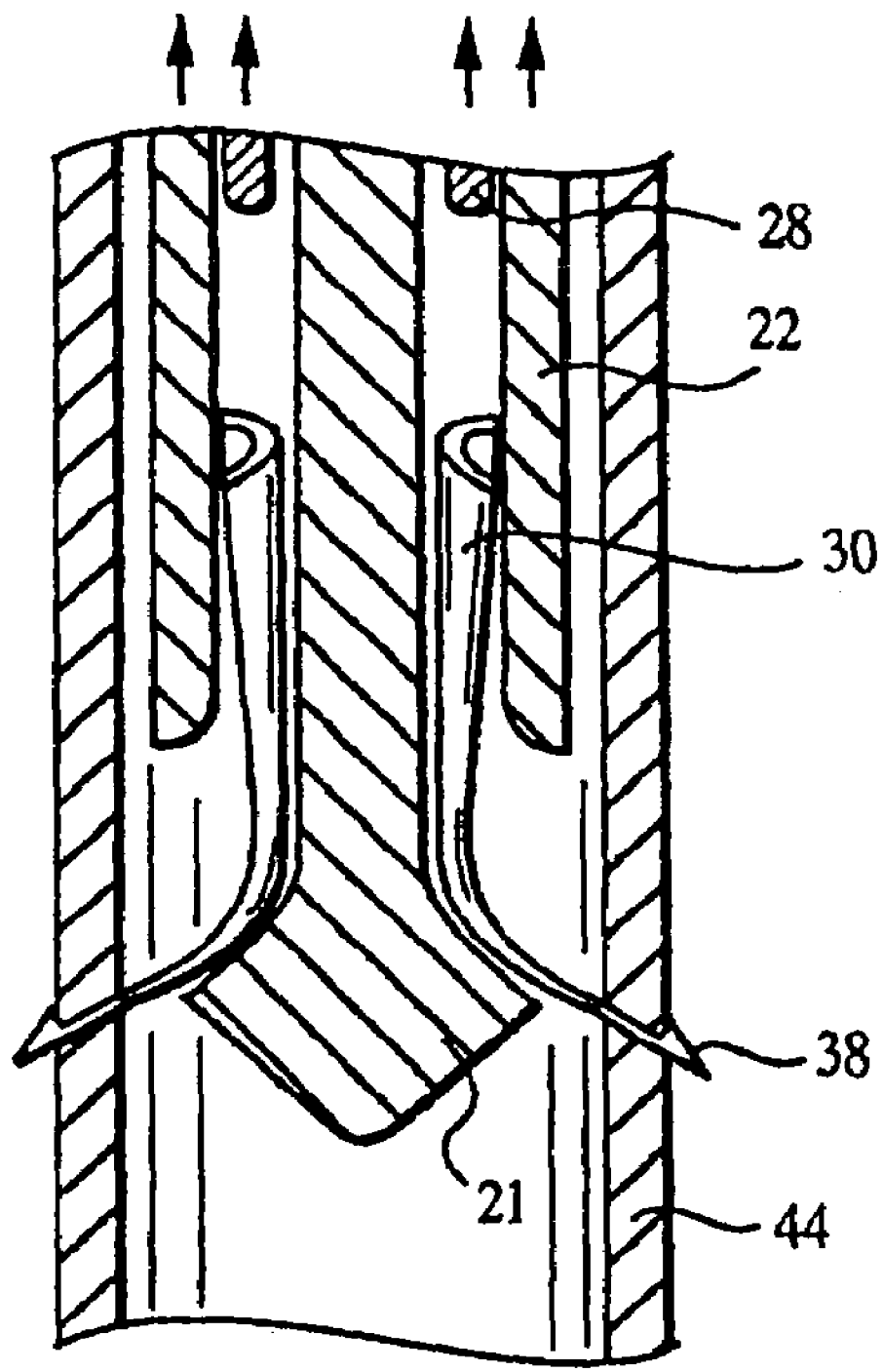
Figure 5E:
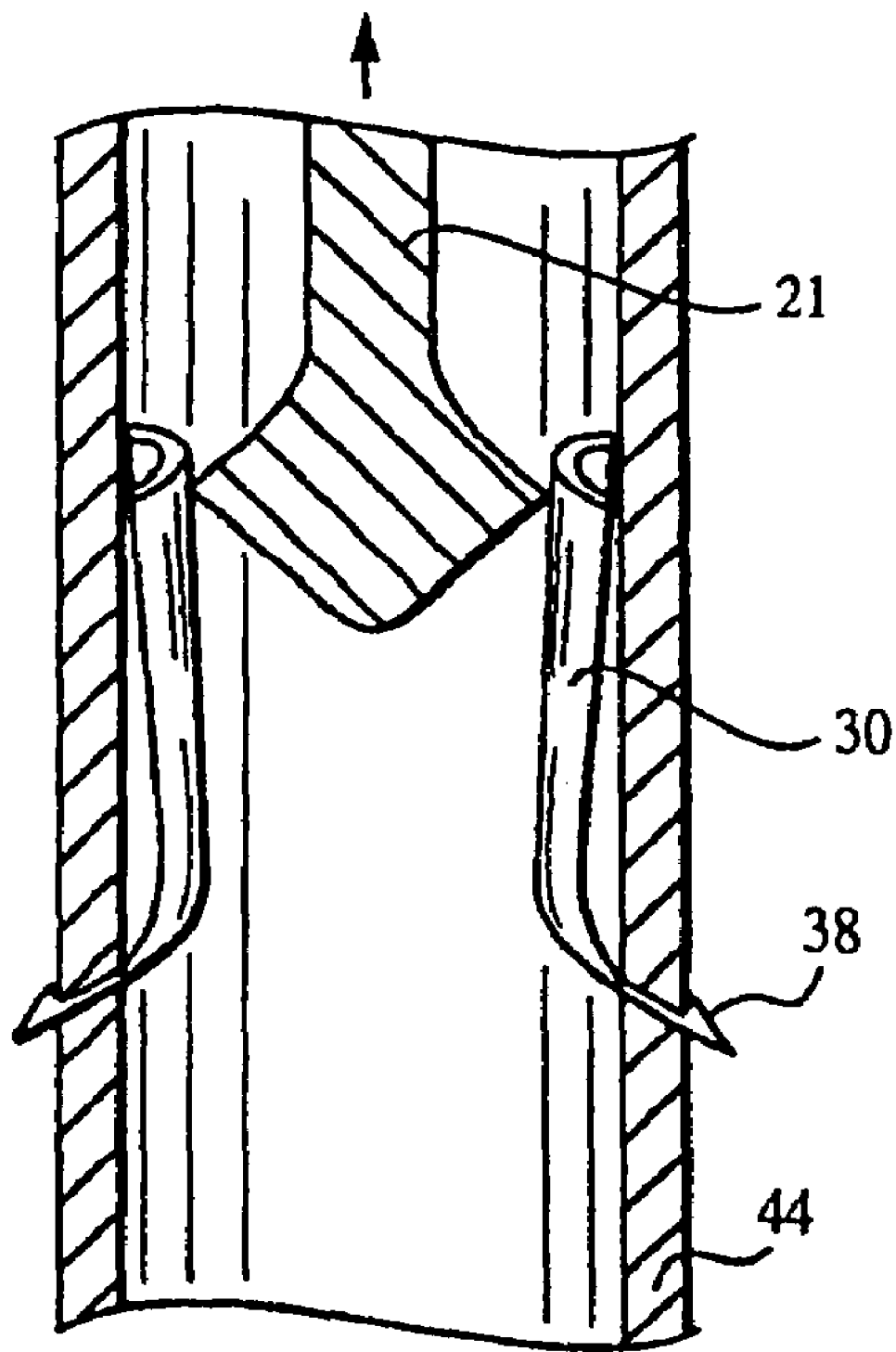

After each cusp 30 is secured to the vessel 46, the retractable sheath 22 is retracted to fully expose the cusps 30 (FIG. 5D). The central portion 21 is then pulled proximally past the flexible (and deflectable) cusps 30 and retracted from the vessel 46 (FIG. 5E). The cusps 30, now secured to the wall 44, can deform between the first and second positions, as described above.

Cusps 30 are preferably made of a biocompatible material capable of reversible deformation as described above. Each cusp 30 can be formed from a thin, flexible material, such as a polyurethane, polyethylene or fluoroplastic, for example, polytetrafluoroethylene (PTFE). Invertible portion 42 can be formed of one or more materials. For example, invertible portion 42 may include an edge portion that is relatively more flexible or more compliant than another portion of the invertible portion to help the edges meet and seal when the cusps 30 are in the second position. Cusps 30 can include a radiopaque material, such as a polymer including a radiopacifier, e.g., tantalum metal or bismuth oxychloride, for positioning and monitoring the cusps.

Similarly, anchoring element 38 is preferably biocompatible. The anchoring element 38 can be formed of a relatively rigid material, such as a polymer having suitable hardness, for example, acrylonitrile-butadiene-styrene (ABS). Other materials can be used, such as metals (e.g., tantalum, tungsten or gold), alloys (e.g., stainless steel or Nitinol), and ceramics. Anchoring elements 38 can include a radiopaque material for positioning and monitoring cusps 30. The anchoring element can be embedded in the invertible portion or fixed to a surface of the invertible portion with, for example, adhesive.

OTHER EMBODIMENTS

Figure 6A:
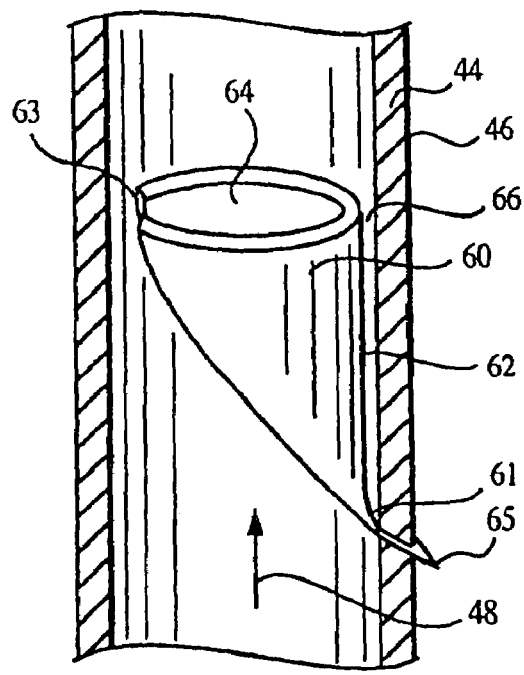
FIGS. 6A and 6B are partial perspective views of an embodiment of a valve cusp.
Figure 6B:
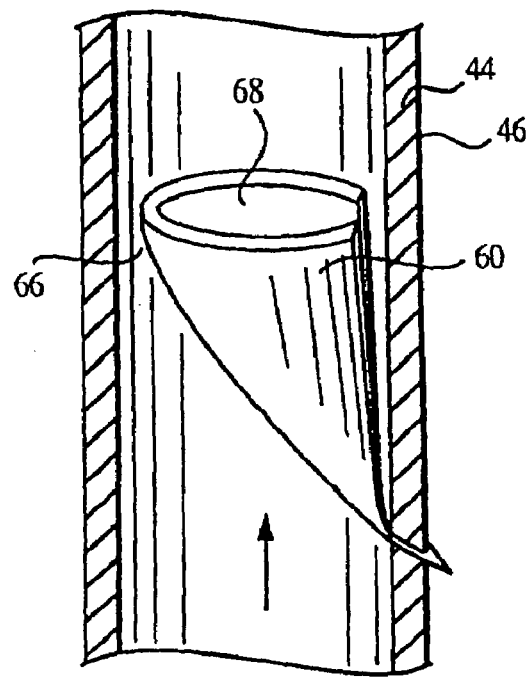

In other embodiments, any number of cusps can be anchored to the wall 44 of the vessel 46 to function as a valve for preventing retrograde flow of blood through the blood vessel 46. Referring to FIGS. 6A and 6B, a single cusp 60 can be used. The cusp 60 can be 10 transported to the treatment site and anchored to the wall 44 of a vessel 46 in the same manner as described above using a catheter. In a first position, the cusp 60 forms an approximate semi-cone, with the edges 63 of the semi-cone facing the wall 44 opposite from where the cusp 60 is anchored to the wall 44. The interior of the cone forms a channel 64 allowing fluid flow past the cusp 60. The anchoring element 65 holds the cusp 30 slightly away from the wall 44 such that a gap 66 is formed between the cusp 60 and the wall 44. Retrograde flowing fluid can accumulate in the gap 66 and exert pressure on the cusp 60, deforming the cusp 60 and widening the gap 66 until the pressure on the cusp 60 inverts the cusp. Referring particularly to FIG. 6B, in an inverted position the cusp 60 forms an approximate cone with the wall 44 and accumulates retrograde flowing fluid in a sack 68 formed by the interior of the cone. Accumulated fluid can exert pressure on the cusp 60, causing the cusp 60 to move away from the wall 44. As a result, the space 66 between the cusp 60 and the wall 44 opposite the anchoring element narrows, until the cusp 60 touches the wall 44, in a second position as shown. In the second position, flow is reduced past the cusp 60 relative to the flow when the cusp 60 was in the first position. The cusp 60 remains in the second position until pressure exerted on the cusp 60 by the antegrade flow of fluid is sufficient to invert the cusp 60 to the first position.

Figure 7A:
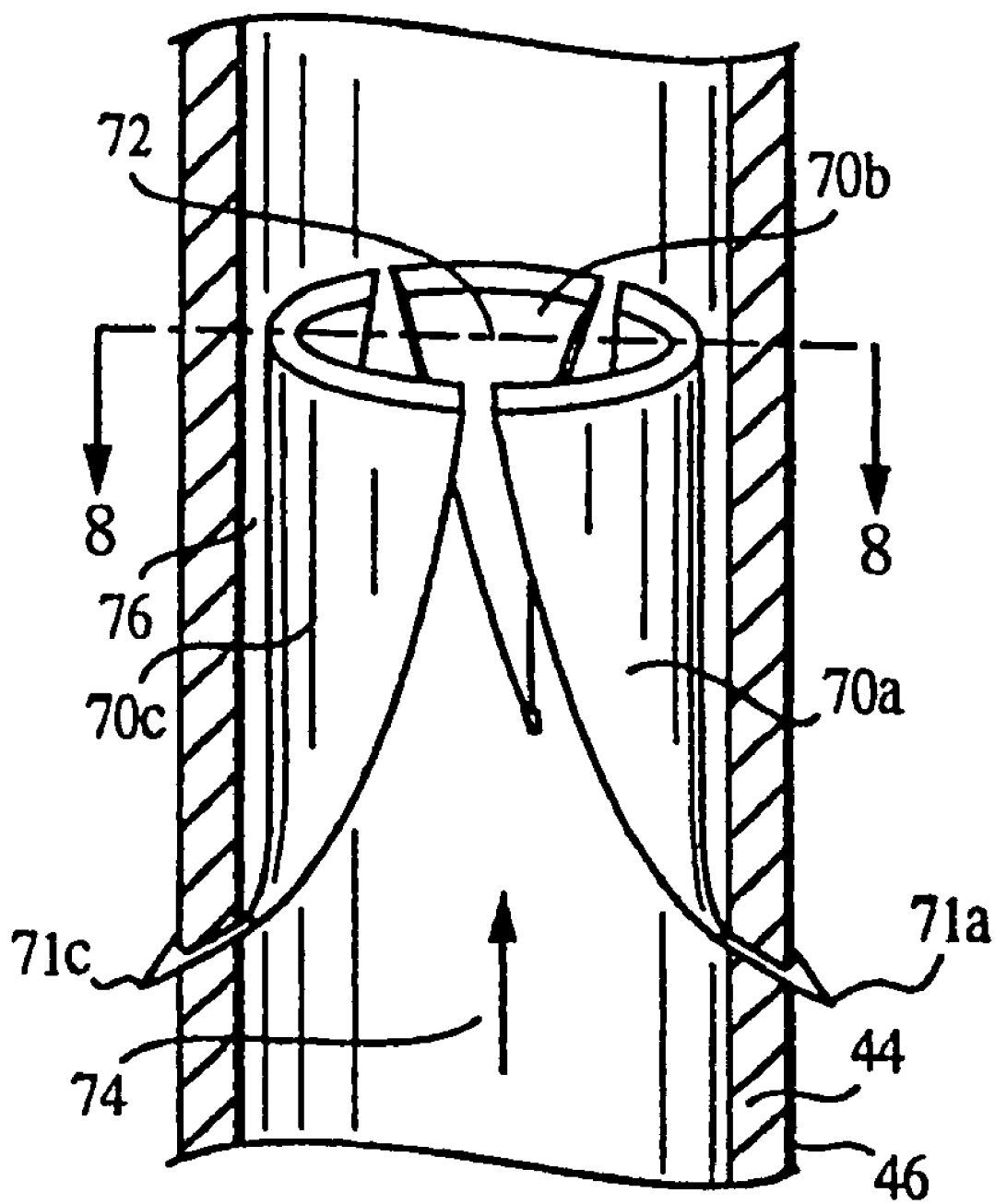
FIGS. 7A and 7B are partial perspective views of an embodiment of a valve cusp.
Figure 7B:
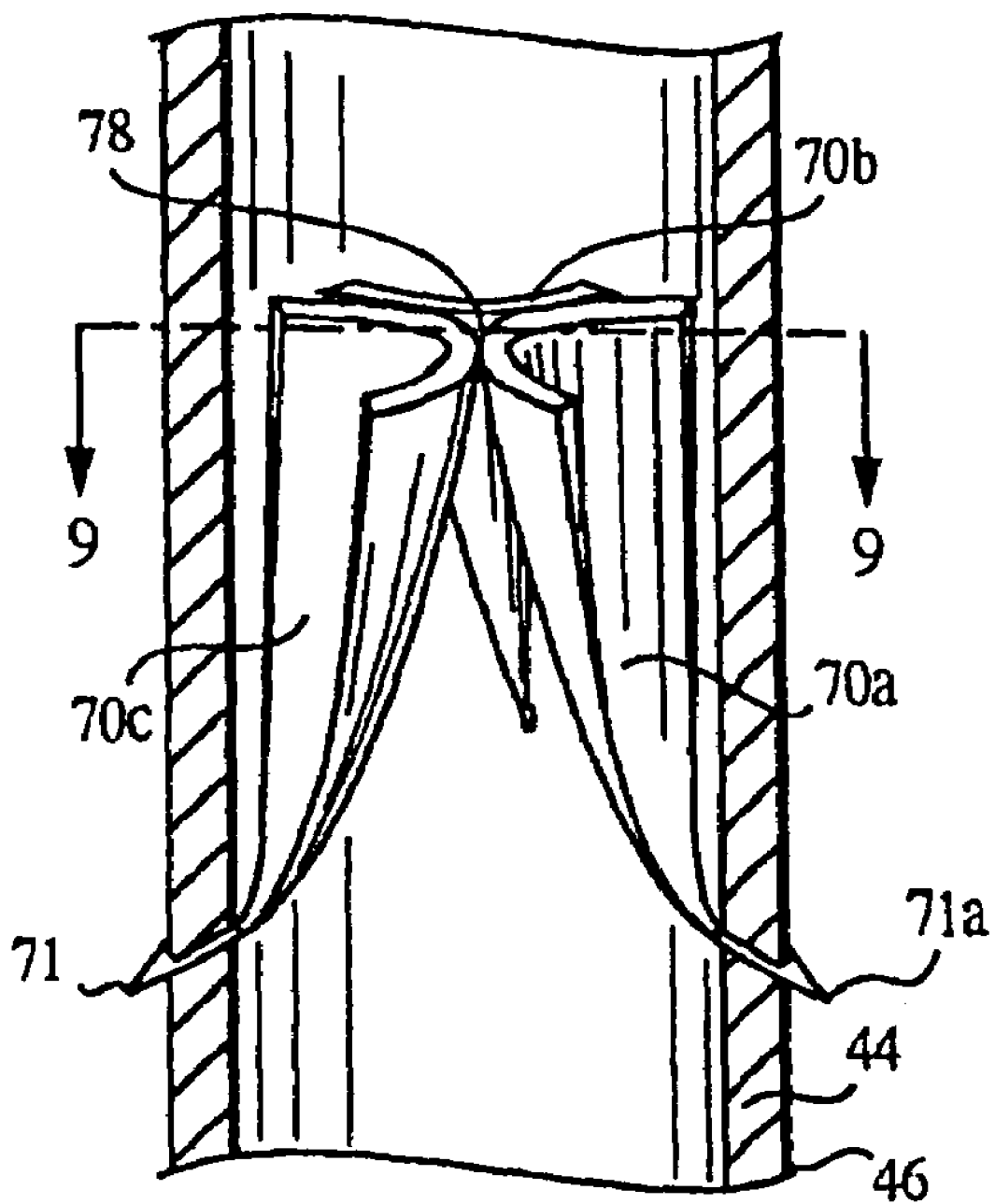
Figure 8:
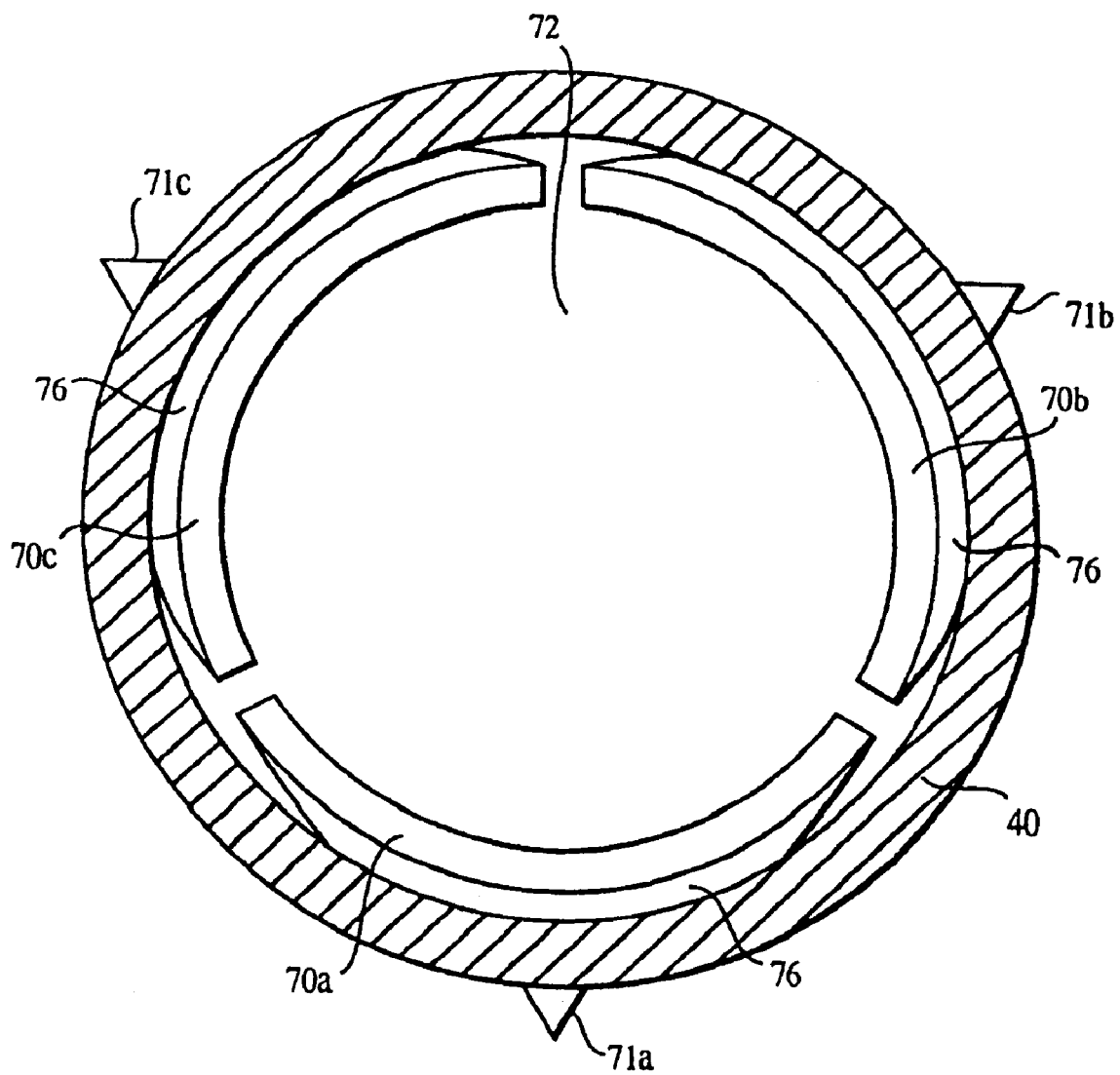
FIG. 8 is a cross-sectional view of the valve cusp of FIG. 7A, taken along line 8-8.

Referring to FIGS. 7A-7B, three cusps 70a-70c can be symmetrically secured to the wall 44 of a vessel 46 in a similar manner as described above. Referring particularly to FIG. 7A, the cusps 70a-70c are shown in first position that does not substantially impede flow of a fluid through the vessel 46. As shown in FIG. 8, the surfaces of the cusps 70a-70c conform to the wall 44 of the vessel 46, allowing a substantial opening 72 for flow past the cusps 70a-70c. Each cusp 70a-70c is held away from the wall 44 by anchoring elements 71a-71c, such that a gap 76 is formed between each cusp and the wall 44. As described above, retrograde flowing fluid accumulates in the gap 76 and exerts pressure on the cusp 70, causing the cusp to deform away from the wall 44, until the cusps invert.

Figure 9:
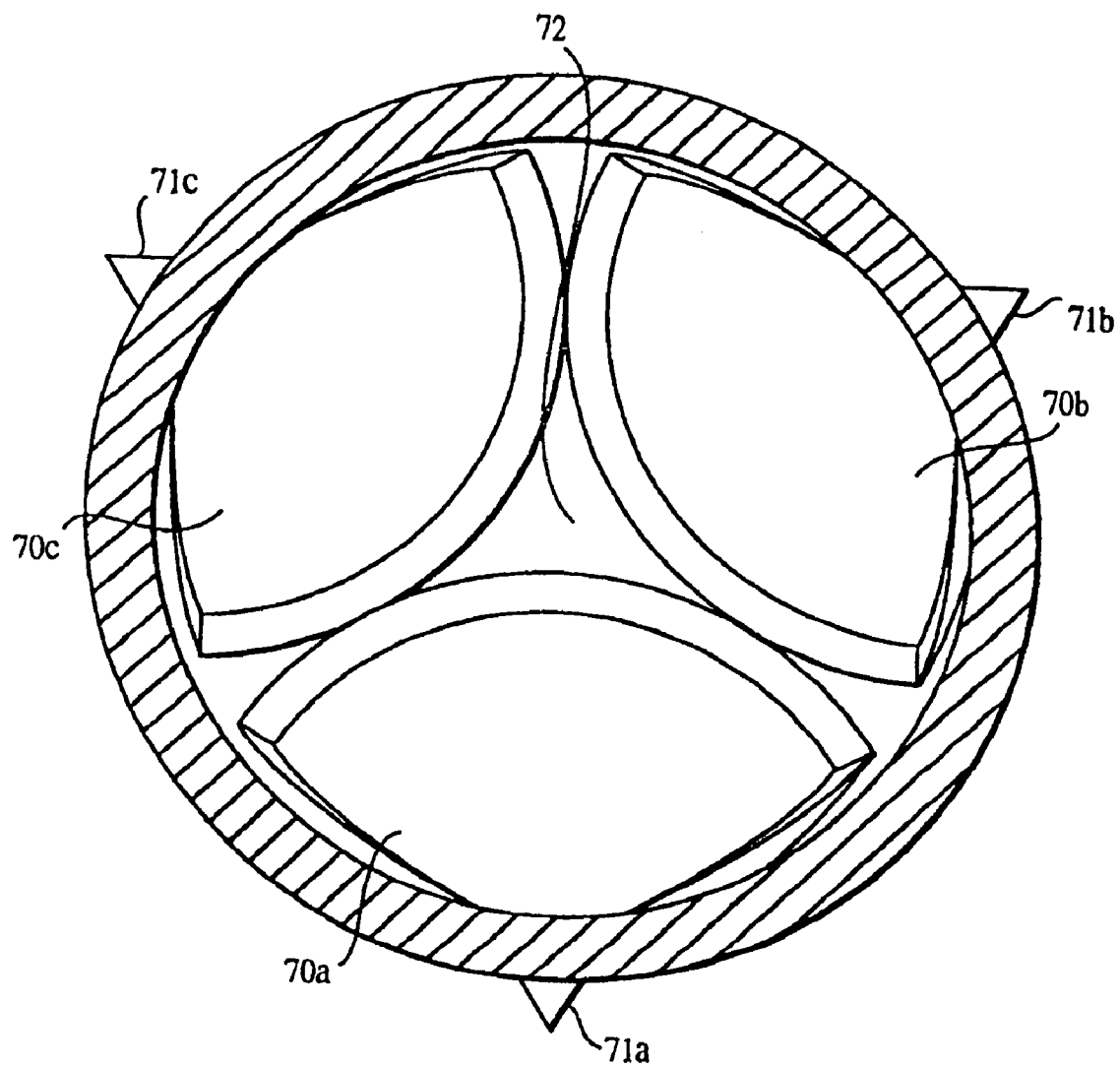
FIG. 9 is a cross-sectional view of the valve cusp of FIG. 7B, taken along line 9-9.

Referring particularly to FIG. 7B, in an inverted position the interior of each cusp 70a-70c accumulates retrograde flowing fluid. Exerting pressure on the cusps causes them to move toward one another, until the cusps 70a-70c meet in a second position and reduce flow past the cusps 70a-70c relative to the when the cusps 70a-70c are in the first position. Referring to FIG. 9, the opening 72 is significantly reduced, thus restricting the fluid flow. The cusps 70a-70c remain in the second position until pressure exerted on the cusps 70a-70c by antegrade flow of fluid inverts the cusps to the first position.

Although the embodiments above describe a device having one to three cusps, any number of cusps can be used to prevent retrograde flow through a vessel. The cusps can be arranged symmetrically as shown, or can be arranged in any other configuration. Although the embodiments described above included cusps of similar size and configuration, cusps of differing sizes and configurations can be used in conjunction with each other.

Figure 10:
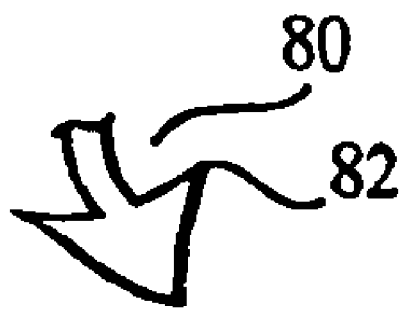
FIG. 10 is a partial perspective view of an embodiment of an anchoring element.
Figure 11:
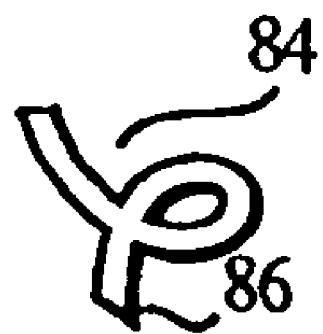
FIG. 11 is a partial perspective view of an embodiment of an anchoring element.

The anchoring element can take a number of different forms that permit the end of the cusp to penetrate the wall of a blood vessel and restrain the end of the cusp from re-entering the vessel. For example, the anchoring element can be a barb element, as shown in the embodiments described above. Alternatively, the anchoring element can be a T-hook device 80 as shown in FIG. 10, wherein T-hook 80 penetrates the wall of a vessel and hooks 82 prevent the anchor from re-entering the vessel. In another embodiment, the anchoring element can define a loop 84, as shown in FIG. 11, wherein the looped end 86 prevents the anchor from re-entering the vessel.

In other embodiments, a cusp can include more than one anchoring element. A cusp can have other polygonal configurations. For example, a generally rectangular cusp can be secured to a vessel using two anchoring elements adjacent to two corners of the cusp. The cusp can form a semi-cylinder.

Other embodiments are within the scope of the following claims.

What is claimed is:

1. A medical device, comprising:
    a first frameless membrane not supported by a frame having a first membrane sealing surface; and
    a second frameless membrane not supported by a frame having a second membrane sealing surface, the first frameless membrane and the second frameless membrane implantable in a body lumen and deformable between a first position under antegrade fluid flow and a second position under retrograde fluid flow, where in the second position the first membrane sealing surface and the second membrane sealing surface meet to resist fluid flow, and where the first membrane sealing surface and the second membrane sealing surface are formed of a material different from and more flexible than other portions of the first frameless membrane and the second frameless membrane.

2. The medical device of claim 1, where the first frameless membrane and the second frameless membrane are symmetrically implantable in the body lumen.

3. The medical device of claim 1, where the first frameless membrane and the second frameless membrane each include at least one anchoring element.

4. The medical device of claim 3, where the anchoring element is configured to embed within the body lumen.

5. The medical device of claim 3, where the anchoring element is configured to penetrate through the body lumen.

6. The medical device of claim 1, where the first frameless membrane and the second frameless membrane include a radiopaque material.

7. The medical device of claim 1, where the first membrane sealing surface and the second frameless member sealing surface include a radiopaque material.

8. The medical device of claim 1, where the first frameless membrane and the second frameless membrane each define a portion of a cone.

9. The medical device of claim 8, where the first frameless membrane and the second frameless membrane each include an anchoring element adjacent to a vertex of the cone.

10. The medical device of claim 1, where the first frameless membrane and second frameless membrane move from the second position to the first position when antegrade fluid flow exerts a sufficient amount of pressure on the first frameless membrane and second frameless membrane.

* * * * *